United States Patent [19]

Gennari

[11] Patent Number: 4,465,672
[45] Date of Patent: Aug. 14, 1984

[54] STABLE S-ADENOSYLMETHIONINE SALTS, THE PROCESS FOR THEIR PREPARATION, AND THERAPEUTIC COMPOSITIONS WHICH CONTAIN THEM AS ACTIVE PRINCIPLE

[75] Inventor: Federico Gennari, Truccazzano, Italy

[73] Assignee: Bioresearch S.p.A., Milan, Italy

[21] Appl. No.: 408,683

[22] Filed: Aug. 16, 1982

[30] Foreign Application Priority Data

Aug. 24, 1981 [IT] Italy ................ 23602 A/81

[51] Int. Cl.³ .................. A61K 31/70; C07H 19/06
[52] U.S. Cl. ........................... 424/180; 536/26
[58] Field of Search ..................... 536/26; 424/180

[56] References Cited

U.S. PATENT DOCUMENTS

| | | | |
|---|---|---|---|
| 3,893,999 | 7/1975 | Fiecchi | 536/26 |
| 3,954,726 | 5/1976 | Fiecchi | 536/26 |
| 4,057,686 | 11/1977 | Fiecchi | 536/26 |

FOREIGN PATENT DOCUMENTS

| | | | |
|---|---|---|---|
| 53-107485 | 9/1978 | Japan | 26/ |
| 57-192399 | 11/1982 | Japan | 536/26 |
| 2064523 | 6/1981 | United Kingdom | 536/26 |

*Primary Examiner*—Ethel G. Love

*Attorney, Agent, or Firm*—Stevens, Davis, Miller & Mosher

[57] ABSTRACT

New S-adenosylmethionine salts have been prepared which are stable indefinitely with time, even at elevated temperatures.

The new salts correspond to the formula:

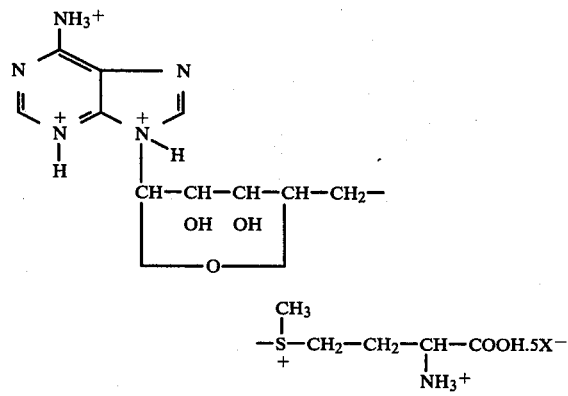

in which X is the equivalent of an organic sulphonic acid of pK less than 2.5, and possess therapeutic activity in numerous fields of human therapy.

2 Claims, No Drawings

STABLE S-ADENOSYLMETHIONINE SALTS, THE PROCESS FOR THEIR PREPARATION, AND THERAPEUTIC COMPOSITIONS WHICH CONTAIN THEM AS ACTIVE PRINCIPLE

This invention relates to a new class of S-adenosylmethionine (SAM) salts which are highly stable at elevated temperatures and for practically indefinite time periods.

It is known that S-adenosylmethionine is a product of natural origin present in all living organisms, in which it is actively synthesised by a specific enzyme, and corresponds to the following structural formula:

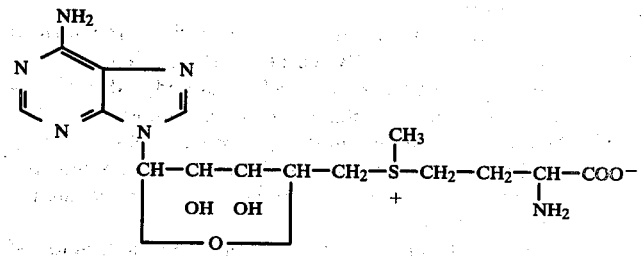

SAM participates in a great number of metabolic processes of fundamental importance for the human organism, and consequently its deficiency lies at the basis of many organic malfunctions.

Although the biological importance of this product has been known for some decades, the possibility of testing it and thus using it as a drug has existed only in recent years, because of its extreme instability at temperatures exceeding 0° C.

In this respect, only in 1975 did the present applicant succeed in preparing a SAM salt which was sufficiently stable at 25° C. (U.S. Pat. No. 3,893,999), followed by some salts having good stability at 45° C. (U.S. Pat. No. 3,954,726/1976 and U.S. Pat. No. 4,057,686/1977).

More specifically, U.S. Pat. No. 3,893,999/1975 describes SAM triparatoluene sulphonate, U.S. Pat. No. 3,954,726/1976 describes SAM disulphatediparatoluene sulphonate, and U.S. Pat. No. 4,057,686/1977 describes a group of SAM salts which can be indicated overall as $SAM.4RSO_3H$ or $SAM.3RSO_3H$ in which $RSO_3H$ indicates a sulphonic acid equivalent which can be partly substituted by the equivalent of sulphuric acid.

The said applicant has stated that he is unable to explain the reason why only the specific claimed salts were stable, when SAM salts prepared under the preceding state of the art (namely the monochloride—U.S. Pat. No. 2,969,353—and disulphate—West German patent application No. 1,803,978) had at the most attained a limited stability with time if maintained at 4° C., nor why triparatoluene sulphonate was stable only up to 25° C., while disulphatediparatoluene sulphonate was stable up to 45° C.

It has now been quite unexpectedly found, and forms the subject matter of the present invention, that stable SAM salts are obtained whenever SAM is salified with 5 moles of an organic sulphonic acid of pK less than 2.5.

More specifically, it has been surprisingly found that if SAM is salified with 5 moles of an organic sulphonic acid of pK less than 2.5, a salt of maximum stability is obtained.

Salts containing 4 or 6 moles of acid have a stability which is still good, but decidedly less. Salts containing 1 to 3 moles of acid are absolutely unacceptable for therapeutic use in that they are subject to vast degradation phenomena.

It must be emphasised that as the new salts according to the invention all find application in human therapy, the presence of even a small percentage of a degraded product is unacceptable not only because it implies a corresponding loss of activity, but also and in particular because it indicates the formation of metabolites which have been found to be slightly toxic and have the capacity to interfere with biological processes.

It has also been found, and represents a further subject matter of the present invention, that the stability of the new SAM salts is directly influenced by the polarity of the environment, and thus in particular by the quantity of moisture present, and means have therefore been found to reduce this moisture to values close to zero.

The salts according to the present invention correspond to the general formula

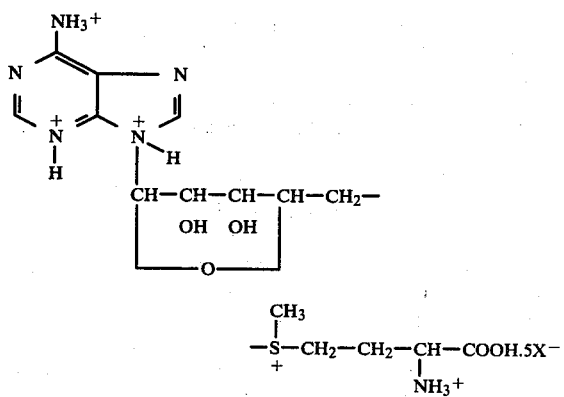

in which X is the equivalent of an organic sulphonic acid of pK less than 2.5.

In particular, it has been found that salts of optimum stability are obtained when X is $CH_3—SO_3^-$ or $CH_3—C_6H_4—SO_3^-$. The pK of these two acids is as follows:

methanesulphonic acid: pK <0.5
p.toluenesulphonic acid: pK <0.5

The new salts have proved very useful in numerous fields of human therapy, for example as hepato-protectors as will be more apparent hereinafter.

They are prepared by a process comprising the following essential stages, which are all critical for the purpose of obtaining a product of absolutely constant and reproducible pharmaceutical purity:

(a) preparing a concentrated aqueous solution of a crude SAM salt by any known method;

(b) purifying the solution by chromatography, by passage through a weakly acid ion exchange resin column;

(c) eluting the SAM with a dilute aqueous solution of the required acid;

(d) titrating the eluate and adjusting the acid quantity to the strictly stoichiometric proportion relative to the SAM present;

(e) concentrating the eluate;

(f) lyophilisation.

The aqueous solution prepared in stage (a) can obviously contain any soluble SAM salt because the anion is eliminated in the next passage through the column, and therefore does not interfere with the rest of the process. In general, with the normal processes involving concentration and extraction of SAM from yeast, a solution is obtained containing the SAM+ ion and the $SO_4^{--}$ ion. In all cases, the pH of the solution is adjusted to between 6 and 7, and preferably 6.5.

The chromatographic purification stage (b) is carried out preferably with Amberlite IRC50 or Amberlite CG50.

The elution of stage (c) is preferably carried out with a 0.1 N aqueous solution of the required acid.

If titration of the eluate (stage d) shows that the quantity of acid equivalents present is less than 5, this being the usual case, then that quantity of acid corresponding exactly to the deficiency is added in the form of a concentrated commercial aqueous solution. However, if it is shown that an excess of acid is present, this is eliminated by treating the solution with strong basic ion exchange resin in $OH^-$ form, for example Amberlite IRA-401.

In stage (e), the eluate is concentrated to an optimum value for the subsequent lyophilisation process, i.e. to a value of between 50 and 100 g/l, and preferably around 70 g/l.

The final lyophilisation is carried out by the usual methods, to give a perfectly crystalline salt of 100% purity.

If lyophilisation is carried out in the presence of a suitable inert substance, a product is obtained having a smaller residual moisture content, and thus more stable.

More specifically, it has been found that if the prepared salt is intended for use in injectable pharmaceutical forms, lyophilisation should be carried out in the presence of mannitol. If however the new salt is intended for the preparation of oral tablets, lyophilisation should be carried out in the presence of powdered silicic acid.

Some practical preparation examples are given hereinafter for purely illustrative purposes, in order to make the new products more easily reproducible.

EXAMPLE 1

110 l of ethyl acetate and 110 l of water are added at ambient temperature to 900 kg of yeast enriched with SAM (6.88 g/kg) in accordance with Schlenk (Enzymologia, 29, 283 (1965)).

After energetically stirring for 30 minutes, 500 l of 0.35 N sulphuric acid are added, and stirring is continued for a further one and a half hours.

The mixture is filtered and the residue washed with water to give 1400 l of solution containing 4.40 g/l of SAM, equivalent to 99.5% of that present in the starting material.

A solution of 11.5 kg of picrolonic acid in 120 l of n-butanol is added to 700 liters of this solution under stirring.

After leaving overnight, the precipitate is separated by centrifuging and washed with water.

The precipitate is dissolved by stirring it at ambient temperature into 31 liters of a 1 N solution of sulphuric acid in methanol.

250 l of benzene are then added.

After the precipitate has completely sedemented, the supernatant solution is decanted, and the insoluble residue is washed with a little ether.

The precipitate is dissolved in 400 l of distilled water, 1 kg of decolourising charcoal are added, and the mixture filtered.

A column of Amberlite IRC 50 resin in $H^+$ form is prepared and carefully washed with distilled water.

4.8 kg of glacial acetic acid are added under stirring to the previously obtained aqueous solution, and 2 N NaOH is then added until a pH of 6.5 is obtained.

The solution is passed through the resin column at a rate of 400 l/h, which is maintained constant during the entire process.

200 l of distilled water, 1600 l of 0.1 M acetic acid and a further 200 l of distilled water are then passed through successively.

The SAM from the ion exchange column is eluted with 200 l of a 0.1 N solution of methanesulphonic acid.

The eluate is concentrated under vacuum to 30 l, after which a sufficient quantity of methanesulphonic acid is added until a molar methanesulphonic acid/SAM ratio of 5:1 is obtained, and the solution is then lyophilised.

4 kg of product are obtained having the following composition: SAM+ 44.7%; $CH_3SO_3H$ 53.8%; $H_2O$ 1.5%.

The product is soluble to the extent of more than 20% in water, but is little soluble in common organic solvents.

Thin layer chromatography shows that the compound is free from any impurity.

The analytical data are as follows:

| empirical formula: $C_{20}H_{42}N_6O_{20}S_6.0.5H_2O$ | | | |
|---|---|---|---|
| | N % | S % | SAM % |
| calculated | 9.47 | 21.65 | 44.9 |
| found | 9.41 | 21.68 | 44.7 |
| E 1% 256 nm = 164 (6N $H_2SO_4$). | | | |

On repeating the process in an identical manner, but using p-toluenesulphonic acid for the column elution, it is possible to obtain a salt of formula:

of which the analytical data are as follows:

| empirical formula: $C_{50}H_{62}N_6O_{20}S_6.0.5H_2O$ | | | |
|---|---|---|---|
| | N % | S % | SAM % |
| calculated | 6.63 | 15.15 | 31.4 |
| found | 6.81 | 15.43 | 31.5 |
| E 1% 256 nm = 115 | | | |

-continued

| empirical formula: $C_{50}H_{62}N_6O_{20}S_6.0.5H_2O$ | | | |
|---|---|---|---|
| | N % | S % | SAM % |
| (6N $H_2SO_4$). | | | |

EXAMPLE 2

The procedure described in Example 1 is followed exactly as far as the column elution.

The SAM is eluted with an aqueous 0.5 N methanesulphonic acid/0.5 N sulphuric acid solution.

After concentrating under vacuum and filtering with activated carbon, the solution is titrated and the two acids are added in an exactly measured quantity to obtain the salt $SAM.1.5H_2SO_4.2CH_3SO_3H.0.5H_2O$.

This salt is obtained with pharmaceutical purity by lyophilisation of the solution.

Its analytical data are as follows:

| empirical formula: $C_{17}H_{33}N_6O_{17}S_{4.5}.0.5H_2O$ | | | |
|---|---|---|---|
| | N % | S % | SAM % |
| calculated | 11.26 | 19.30 | 53.4 |
| found | 11.13 | 18.98 | 53.3 |
| E 1% 256 nm = 195 (6N $H_2SO_4$) | | | |

All possible mixed salts can obviously be prepared by varying the ratio of the two acids.

On repeating the process in an identical manner but using p.toluenesulphonic acid/sulphuric acid mixtures for the elution, the following double salt is obtained: $SAM.1.5H_2SO_4.2CH_3—C_6H_4—SO_3H.0.5H_2O$ of which the analytical data are as follows:

| empirical formula: $C_{29}H_{41}N_6O_{17}S_{4.5}H_2O$ | | | |
|---|---|---|---|
| | N % | S % | SAM % |
| calculated | 9.35 | 16.04 | 44.3 |
| found | 9.27 | 15.95 | 44.1 |
| E 1% 256 nm = 162 (6N $H_2SO_4$) | | | |

It is also possible to obtain an entire series of mixed salts in this case, by varying the ratio of the two added acids.

EXAMPLE 3

The preparation described in example 1 was repeated identically, but 2.50 kg of apyrogenic mannitol were added to the solution before lyophilisation.

The solution was then lyophilised in the usual manner.

The addition of mannitol as a lyophilisation support enables a product to be obtained having a residual moisture content of 0.1%.

The product obtained in this manner is suitable for conversion into injectable pharmaceutical forms.

EXAMPLE 4

The procedure of Example 1 is followed. 2 kg of Aerosil (pulverised silic acid) are added to the solution before lyophilisation, and the resultant colloidal suspension is lyophilised.

The addition of Aerosil as a lyophilisation support enables a product to be obtained having a residual moisture content of 0.2%.

The product obtained in this manner is suitable for conversion into tablets for oral use.

Stability tests were carried out at 45° C. on the salts prepared in the described manner, by determining the percentage of residual salt of basic SAM+ at fixed times.

The residual SAM percentage at the times indicated was determined by the new method described hereinafter, which ensures maximum accuracy of measurements in that it enables the SAM to be totally separated from all possible degradation products.

In this respect, it has been found that with the method used up to the present time, based on an analytical column of Dowex 50 ion exchange resin (Schlenk and De Palma: J. Biol. Chem. 229 (1957)), the separation of the SAM from certain degradation products, and in particular from methylthioadenosine, was not complete and therefore led to an error in evaluating the stability of the SAM, which appeared better than it was.

The present method for determining the SAM is based on the use of HPLC.

Analytical conditions used:
column: PARTISIL 10 SXC−2.5×250 mm
eluent: 0.1 M ammonium formate of pH 4, containing 20% of methanol for HPLC
flow: 1 ml/minute
SAM retention time: about 400 seconds.

TABLE 1

| | SAM.n $CH_3SO_3H$ | | | | |
|---|---|---|---|---|---|
| | DEGRADATION AT 45° C. AFTER | | | | |
| | residual | 60 | 120 | 180 | 240 | 360 |
| n | moisture | days | days | days | days | days |
| 1 | 0.2% | 100% | 100% | 100% | 100% | 100% |
| 2 | 0.5% | 80% | 100% | 100% | 100% | 100% |
| 3 | 0.8% | 30% | 60% | 80% | 100% | 100% |
| 4 | 1% | 5% | 10% | 14% | 17% | 20% |
| 5 | 1.5% | — | 1.5% | 3% | 4.5% | 5% |
| 6 | 2% | 5% | 10% | 14% | 17% | 20% |

TABLE 2

$$SAM.n\ CH_3\text{—}\!\!\!\bigcirc\!\!\!\text{—}SO_3H$$

| | | DEGRADATION AT 45° C. AFTER | | | | |
|---|---|---|---|---|---|---|
| | residual | 60 | 120 | 180 | 240 | 360 |
| n | moisture | days | days | days | days | days |
| 1 | 0.2% | 100% | 100% | 100% | 100% | 100% |
| 2 | 0.5% | 80% | 100% | 100% | 100% | 100% |
| 3 | 0.8% | 30% | 60% | 80% | 100% | 100% |
| 4 | 1% | 5% | 10% | 14% | 17% | 20% |
| 5 | 1.5% | — | 1.5% | 3% | 4.5% | 5% |
| 6 | 2% | 5% | 10% | 14% | 17% | 20% |

TABLE 3

| | SAM.1.5 $H_2SO_4$.n $CH_3SO_3H$ | | | | |
|---|---|---|---|---|---|
| | DEGRADATION AT 45° C. AFTER | | | | |
| | residual | 60 | 120 | 180 | 240 | 360 |
| n | moisture | days | days | days | days | days |
| 1 | 1% | 5% | 10% | 14% | 17% | 20% |
| 2 | 1.5 | — | 1.5% | 3% | 4.5% | 5% |
| 3 | 2% | 5% | 10% | 14% | 17% | 20% |

TABLE 4

SAM.1.5 $H_2SO_4$ n $CH_3$—C$_6$H$_4$—$SO_3H$

| n | residual moisture | DEGRADATION AT 45° C. AFTER | | | | |
|---|---|---|---|---|---|---|
| | | 60 days | 120 days | 180 days | 240 days | 360 days |
| 1 | 1% | 5% | 10% | 14% | 17% | 20% |
| 2 | 1.5% | — | 1.5% | 3% | 4.5% | 5% |
| 3 | 2% | 5% | 10% | 14% | 17% | 20% |

From the data of tables 1, 2, 3 and 4 it is apparent that, completely unforeseeably, SAM salts attain maximum stability when they contain 5 acid equivalents. Salts with 4 or 6 equivalents still have good stability, whereas salts with a lower number of acid equivalents have no practical use because of their instability.

It is also apparent that the stability takes the same pattern independently of the acid used, provided that it is an organic sulphonic acid of pK<2.5.

It was not possible to prepare salts with acids of pK>2.5 containing 4 to 6 acid equivalents.

Stability tests were also carried out by the same method on salts prepared in the presence of a lyophilisation support, in accordance with examples 3 and 4.

The results of these determinations are given in the following tables 5 and 6. The drastic reduction in moisture content when lyophilisation is carried out in the presence of a support is apparent, together with the consequent total stability of the salts which is attained in this manner.

TABLE 5

SAM.5CH$_3$SO$_3$H

| | RESIDUAL MOISTURE | DEGRADATION AT 45° C. AFTER 360 DAYS |
|---|---|---|
| Lyophilised without support | 1.5% | 5% |
| Lyophilised with mannitol (100 g SAM$^+$ + 120 g mannitol) | 0.1% | — |
| Lyophilised with Aerosil (100 g SAM$^+$ + 100 g Aerosil) | 0.2% | — |

TABLE 6

SAM.5CH$_3$—C$_6$H$_4$—SO$_3$H

| | RESIDUAL MOISTURE | DEGRADATION AT 45° C. AFTER 360 DAYS |
|---|---|---|
| Lyophilised without support | 1.5% | 5% |
| Lyophilised with mannitol (100 g SAM$^+$ + 120 g mannitol) | 0.1% | — |
| Lyophillised with Aerosil (100 g SAM$^+$ + 100 g Aerosil) | 0.2% | — |

The salts SAM.5CH$_3$SO$_3$H and SAM.5CH$_3$—C$_6$H$_4$—SO$_3$H were tested in a wide pharmacological screening trial, and in all cases showed highly interesting activity and toxicity characteristics which were independent of the anion bonded to the SAM. It was established that the activity of the new salts depends substantially on the capacity of the SAM$^+$ ion released in the organism to act as a donor of methyl groups, as the natural substrate of a large number of transmethylase enzymes which catalyse fundamental reactions of the lipid, protide and glucide metabolism.

The importance of the new salts thus derives substantially from the fact that they make the S-adenosylmethionine absolutely stable at temperatures up to 45° C., so enabling its transmethylating activity in the human organism to be utilised 100% without the risk of formation of toxic degradation products which interfere negatively with the biological processes activated by the SAM$^+$.

Toxicity

The acute toxicity in the mouse was determined, the following values being obtained for both salts:

LD$_{50}$ by oral administration >3 g/kg
LD$_{50}$ by intravenous administration 1.1 g/kg Tolerability and chronic toxicity tests were carried out on rats of the Wistar and Sprague-Dowley stock, by administering 20 mg/kg per day of product for 12 months. On termination of the treatment, the various organs and systems showed no pathological alteration.

Teratogenesis tests were carried out on rabbits. When salt doses ten times greater than the maximum therapeutic doses were administered, no teratogenic action or malformative action on the embryos or terminal fetuses was encountered.

Intravenous administration of doses up to 200 mg/kg caused no pyrogenic manifestation in the rabbit.

Venous administration of 40 mg/kg in the rabbit and rat caused no change in carotid pressure, cardiac and respiratory frequency, or in the electrocardiograph trace.

Local tolerability of intramuscular injection, even after administrations repeated for 30–60 days, and of intravenous injection in the marginal vein of the outer ear of the rabbit, was excellent.

Pharmacology

An entire series of tests carried out on rats have shown that the new salts exert a very considerable protective and resolving action in hepatic steatosis induced by a hyperlipid-hyperprotein diet in accordance with Handler, and in steatosis induced by acute alcoholic intoxication and other toxic agents even when administering doses of 10 mg/kg of SAM$^+$.

In experimental hyperlipemia in the rat, for example induced by Triton S, the new salts have demonstrated a very conspicuous hypolipemic activity which, in relation to the dose used, i.e. 10 mg/kg (again expressed in SAM$^+$), was much more intense than in the case of other drugs of hypolipemic activity.

In chickens rendered atherosclerotic by means of diets enriched in cholesterol and fructose, parenteral administration of the new product in doses of 10 mg/kg reduced the cholesterolemia and favourably modified lesions encountered in the controls with respect to the thoracic and abdominal aorta and the small vessels of the encephalic base.

With regard to phospholipid metabolism, it was found experimentally that there was an increase in the phosphatidylcholine quantity in the hepatic tissue of rats with uncompensated steatosis. A clear increment in the phosphatidylcholine was also determined at the expense of the hematic α-lipoproteins in experimental alterations caused by β/α lipoprotein ratios.

All these tests have clearly indicated a curative effect of the new salts in alterations of the lipid metabolism.

A further series of tests carried out on the rat have shown that administration of 1 mg/kg doses induces an accumulation of glycogenic reserves at the hepatic and muscular level, which is demonstrated both by histochemical methods and by quantitative determinations. In experimental diabetes induced by alloxan, the insulin quantity necessary for returning glycemia values to normal was considerably reduced by administrations equivalent to 0.5 mg/kg of SAM+.

This series of tests has demonstrated a clear positive action of the new compounds according to the invention on the glucide metabolism.

Finally, rats with experimentally induced hypodisproteinemia were treated with quantities of 10 mg/kg of SAM. It was found that said product returns the total proteinemia values to normal, by substantially increasing the albumin level and thus showing marked protein anabolic activity.

This and other similar tests have demonstrated the curative power of the new products in malfunctions of the protide metabolism.

Summarising, on the basis of the aforesaid pharmacological tests and of many others which have enabled the activity of the new salts to be explored at all levels in the human organism, the activity of the new products has been clinically established in hepatology in the case of acute and chronic hepatic intoxication, in neurology as an antidepressive, and in osteology in the case of rheumatoid arthritis.

The activity in numerous other fields of human therapy is under investigation.

The new salts can be administered orally, or by intramuscular or intravenous injection.

Other possible administration forms are suppositories, liquids for ocular installation, aerosol, or forms for topical application.

I claim:

1. S-adenosylmethionine (SAM) salts of formula:

[chemical structure]

in which X is the acid equivalent of an organic sulphonic acid of pK less than 2.5.

2. A composition for the treatment of hyperlipemia comprising an anti-hyperlipemic effective amount of the compound of claim 1 and a therapeutically acceptable carrier.

* * * * *